US007511005B2

(12) United States Patent
Jones et al.

(10) Patent No.: US 7,511,005 B2
(45) Date of Patent: Mar. 31, 2009

(54) LIPOLYTIC ENZYME ELIP

(75) Inventors: Brian E Jones, Palo Alto, CA (US);
William D. Grant, Palo Alto, CA (US);
Shaun Heaphy, Palo Alto, CA (US);
Susan Grant, Palo Alto, CA (US);
Helen C. Rees, Palo Alto, CA (US)

(73) Assignee: Danisco US Inc., Genencor Division, Palo Alto, CA (US)

( * ) Notice: Subject to any disclaimer, the term of this patent is extended or adjusted under 35 U.S.C. 154(b) by 106 days.

(21) Appl. No.: 10/555,587

(22) PCT Filed: May 12, 2004

(86) PCT No.: PCT/US2004/014685

§ 371 (c)(1),
(2), (4) Date: Mar. 8, 2007

(87) PCT Pub. No.: WO2004/101760

PCT Pub. Date: Nov. 25, 2004

(65) Prior Publication Data

US 2007/0259399 A1 Nov. 8, 2007

Related U.S. Application Data

(60) Provisional application No. 60/470,069, filed on May 12, 2003.

(51) Int. Cl.
*A21D 2/00* (2006.01)
*C12N 9/20* (2006.01)
*C07H 21/04* (2006.01)

(52) U.S. Cl. .................. 510/226; 435/198; 536/23.2

(58) Field of Classification Search .............. 435/198; 536/23.2; 510/226

See application file for complete search history.

(56) References Cited

U.S. PATENT DOCUMENTS

| | | |
|---|---|---|
| 4,106,991 A | 8/1978 | Markussen et al. |
| 4,338,397 A | 7/1982 | Gilbert et al. |
| 4,411,994 A | 10/1983 | Gilbert et al. |
| 4,475,056 A | 10/1984 | Hirai |
| 4,513,085 A | 4/1985 | Nakatsukasa et al. |
| 4,513,086 A | 4/1985 | Fayerman et al. |
| 4,661,452 A | 4/1987 | Markussen et al. |
| 4,689,297 A | 8/1987 | Good et al. |
| 4,760,025 A | 7/1988 | Estell et al. |
| 5,217,878 A | 6/1993 | Van Eekelen et al. |
| 5,264,366 A | 11/1993 | Ferrari et al. |
| 5,278,066 A | 1/1994 | Andreoli et al. |
| 5,364,770 A | 11/1994 | Berka et al. |
| 5,514,590 A | 5/1996 | Garvin et al. |
| 5,622,866 A | 4/1997 | Motamedi et al. |
| 5,990,069 A | 11/1999 | Andre et al. |
| 6,255,115 B1 | 7/2001 | Beijersbergen et al. |

FOREIGN PATENT DOCUMENTS

| | | |
|---|---|---|
| WO | WO88/07079 | 9/1988 |
| WO | WO92/06154 | 4/1992 |
| WO | WO92/19709 | 4/1992 |
| WO | WO92/19708 | 11/1992 |
| WO | WO 93/09219 | 5/1993 |
| WO | WO96/18729 A1 | 6/1996 |
| WO | WO 2004/101759 | 11/2004 |
| WO | WO 2004/101763 | 11/2004 |

OTHER PUBLICATIONS

Aunstrup et al., Proc IV IFS: *Ferment. Technol. Today*, 299-305 (1972).
Ausubel et al., eds., Current Protocols in Molecular Biology (1994).
Ausubel et al., eds 1987 Supplement 30, section 7.7.18, Current Protocols in Molecular Biology.
Bajar, Fusarium; Podila and Kolattukudy, 1991, Proc. Natl. Acad. Sci. USA 88: 8202-8212.
Chang et al., *Mol. Gen. Genet.* 168:11-115 (1979).
Cho, AR, et al, *EMS Microbiol Lett*. 186(2):235-238 (2000).
Dartois, V, et al, *Biochim. Biophys. Acta*, 1131(3):253-260 (1992).
DiPietro and Harman, 1993, Curr. Genet. 24: 349-356.
Evan et al., *Molecular and Cellular Biology* 5:3610-3616 (1985).
Fahnestock and Fischer. *J. Bacteriol.* (1986) 165:796-804.
Ferrari et al., Genetics p. 57-72.
Fisher et al., *Arch. Microbiol.* 139:213-217 (1981).
Giliman and Smith, *Gene* 8:81-097 (1979).
Goldman, VanMontagu and Herrera-Estrella, 1990, Curr. Genet. 17:169-174.
Gupta et al, Biotechnol. Appl. Biochem. (2003) 37:63-71.
Hamer and Timberlake, 1984, Proc. Natl. Acad. Sci. USA 81: 1470-1474.
Harwood et al. Ed. "Bacillus", Plenum Publishing Corp. 1989.
Hoch et al., *J. Bacteriol*. 93:1925-1937 (1967).
Holubova, *Folia Microbiol*. 30: 97 (1985).
Hopp et al., *BioTechnology* 6:1204-1210 (1988).
Ilmen, M. et al., Appl. Environ. Microbiol. 63:1298-1306, 1997.
Kieleczawa et al., Science (1992) 258:1787-91.
Lutz-Freyermuth et al., *Proc. Natl. Acad. Sci. USA* 87:6393-6397 (1990).
Mann et al., *Current Microbiol.* 13:131-135 (1986).
Martin et al., *Science* 255:192-194 (1992).
McDonald, *J. Gen. Microbiol.* 130:203 (1984).
Paborsky et al., Protein Engineering 3(6):547-553 (1990).
Penttila, Nevalainen, Ratto, Salminen and Knowles, 1987, Gene 6: 155-164.
Pourquie, J. et al., Biochemistry and Genetics of Cellulose Degradation, eds, 1988.
Roberts et al., *Nature* 328:731-734 (1987).

(Continued)

*Primary Examiner*—Tekchand Saidha

(57) ABSTRACT

The present invention provides a novel nucleic acid sequence, designated ELIP, encoding a lipolytic enzyme and the corresponding encoded amino acid sequences. The invention also provides expression vectors and host cells comprising a nucleic acid sequence encoding at least one novel lipolytic enzyme, recombinant lipolytic enzyme proteins and methods for producing the same.

5 Claims, 5 Drawing Sheets

OTHER PUBLICATIONS

Sambrook et al. Molecular Cloning—A Laboratory Manual (2nd ed.) vol. 1-3, Cold Springs Harbor Publishing (1989).
Sambrook et al., *Molecular Cloning, A Laboratory Manual* (2nd ed. 1989); Kriegler, *Gene Transfer and Expression*.
Sanchez, M, et al, *Biotechnol. Bioeng*. 78(3):339-45 (2002).
Scheider, B., et al., *Protein Expr. Purif* 6435:10 (1995).
Singleton, et al., Dictionary of Microbiology and Molecular Biology, 2D Ed., John Wiley and Sons, New York (1994).
Skinner et al., *J. Biol. Chem*. 266:15163-15166 (1991).
Smith et al., *Appl. and Env. Microbiol*. 51:634 (1986).
Vorobjeva et al., *FEMS Microbiol. Letters* 7:261-263 (1980).
Wang et al., *Gene* (1988) 69:39-47.
Database Embl—Mar. 22, 2001—NF082F11PL1F1093Phosphate starved leaf Medicago truncatula cDNA clone NF082F11PL5, mRNA sequence. >>Datbase accession No. BG45687 Abstract.
Jaeger et al., "Bacterial biocatalysts : molecular biology, three-dimensional structures, and biotechnological applications of lipases." *Annual Review of Microbiology*, (1999) V. 53, pp. 315-351.
The Supplementary European Search Report.

*Figure 1A*

Nucleotide sequence of inserted environmental DNA in clone ELIP (SEQ ID NO:1)

| | | | | | |
|---|---|---|---|---|---|
| TCTATGAGCA | ACAAGGCGGT | TTTAGCGAAG | CGCAGGCCGA | TGAGTTTGTG | 50 |
| GCCGAGGCGC | TGGAAACATT | CCGCTGGCAC | CAGCACGCAA | CGGTTGACGC | 100 |
| CGAAACCTAC | CGCGCGTTGC | ATGATGAGCA | CCGGCTGATC | GCCGATGTAG | 150 |
| TCTGCTTCCG | TGGCTGCCAC | ATTAACCACC | TGACCCCGCG | CACGCTCGAT | 200 |
| ATCGACCGCG | TGCAGTCGCT | GATGCCGGAA | CGCGGAATTA | CCCCAAAAGC | 250 |
| CATTATCGAA | GGGCCGCCGC | GCCGCGAGCG | CCCGATTTTA | CTGCGCCAGA | 300 |
| CCAGCTTTAA | AGCGCTGGAA | GAGCCTATTT | TGTTCGCCGG | TGAGCATCAC | 350 |
| GGAACGCATA | CCGCCCGTTT | CGGCGAAATA | GAACAGCGCG | GCGTAGCGCT | 400 |
| GACGCCGAAA | GGCCGGGCGC | TGTACGACGA | ACTGCTGCTG | GCGGCGGGCA | 450 |
| ACGGCACGGA | TAATCTCAGC | CACCAGCAGC | ATTTACACGA | AGTGTTCACC | 500 |
| GTTTCCCGGA | CAGCGACGCG | CTGCTGCGCC | GCCAGGGGCT | GGCCTATTTC | 550 |
| CGCTATCGTT | TGACGCCCGT | TGGCGAAATG | CACCGCCACT | CAATCAAGCC | 600 |
| AGGCGACGAC | CCGCAGCTGC | TTATAGAACG | CGGCTGGCTG | GTGGCGCAGC | 650 |
| CGGTTATTTA | TGAAGATTTC | CTCCCGGTCA | GCGCGGCGGG | TATTTTCCAG | 700 |
| TCAAACCTTG | GCAGCGACGG | CGGGCAACGG | CAGCACGGCC | ATTCCAGCCG | 750 |
| CAGCGAGTTT | GAACAGGCCC | TTGGCGCAGA | GGTTGCAGAC | GAGTTCGCCC | 800 |
| TCTATCAGCA | GGCCGAGGAT | CGCAGTAAAC | GCCGTTGCGG | TTTGCTGTAA | 850 |
| ACGCGCTACC | CTGCTGGAGT | GTCAGTAACA | AGGAACAGCA | GATGGAACAA | 900 |
| GTTGTTAGCC | GTTGCTCAGG | GGAGACTGAG | CGGCGTTCTT | CAGGGGAAAG | 950 |
| TTGCGGTCTA | TCGCGGCATC | CCCTTTGCCG | CTCCGCCGGT | GGGTGAACTG | 1000 |
| CGCTGGCGGG | CACCTCGTCC | CCCGGCGCAC | TGGCAGGGTA | TCCGCCAGGC | 1050 |
| GGATACATTT | GCGCCTGCAT | GCTGGCAAAG | CCTCGAATAC | TGCAAAGCGG | 1100 |
| TTGGCGGCGG | CGATCCCGGC | CAGTTTTCTG | AAGATTGCCT | GTATCTCAAT | 1150 |
| ATCTGGACCC | CGGCCCGGCG | GGATGCGGAG | CCGCTGCCGG | TTATGGTCTG | 1200 |
| GCTGCACGGT | GGGGGCTACA | CTATCGGCGC | AGGCTCGCTG | CCGCCCTACG | 1250 |
| ATGGAGCAGC | CTTCGCCTCG | CGGGATGTAG | TCCTGGTGAC | GGTGAATTAC | 1300 |
| CGTCTTGGCC | ATCTCGGCTT | TTTCGCCCAT | CCGGCGCTGG | ATGAAGAAAA | 1350 |
| TCCAGACGGC | CCGGTTCATA | ATTTCGCGCT | TTTAGACCAA | ATTGCTGCCC | 1400 |
| TGAAATGGGT | GCAGGAAAAT | ATCGCTGCTT | TCGGCGGCGA | CGCGGGGAAT | 1450 |
| GTCACGCTGT | TTGGCGAGTC | TGCCGGGGCG | CGTAGCGTGC | TTTCGCTGCT | 1500 |
| GGCGTCGCCG | CTGGCGAAAA | ACCTTTTCCA | CAAAGGTATT | ATACAAAGCG | 1550 |
| CCTACACGTT | GCCGGATGTC | GACAGGAAGA | AAGCCCTGAA | ACGTGGCGTA | 1600 |
| GCGCTGGCCG | GTCATTACGG | GCTGCAAAAT | GCCACAGCGG | ATGAACTCCG | 1650 |
| CGCTCTGCCT | GCGGATGGGC | TGTGGGCGCT | TGAAGGGCCG | CTTAACATTG | 1700 |
| GTCCAACGCC | AATCTCCGGC | GACGTCGTGC | TGCCTGAGCC | GATGCTGGAT | 1750 |
| ATATTCTTCG | CCGGGCGTCA | GCACCGCATG | CCCTTGATGG | TCGGGAGCAA | 1800 |
| CAGCGACGAG | GCAAGCGTGC | TGAGCTACTT | CGGCATCGAT | CCTGCCGGGC | 1850 |
| AGGTCGAACT | GCTCGCCGGA | GGAGCGGCGT | TTCCGGACTG | GGGGCTTATC | 1900 |
| AAACTGCTGT | ATTCCGGAG | TGAAANGGGG | ATGCCCGAAC | TCGGCGACA | 1950 |
| GGTGTGCCGC | GATATGGCTT | TTNCCNCGCT | GGGTTTTGTT | GTGATGCAGG | 2000 |
| CCCAGCAGCG | GGTCAATCAG | CCCTGCTGGC | GCTACTATTT | TGATTATGTG | 2050 |
| GGGGAGGCGG | AACGTAAAAT | CTATGCCAAC | GGCACCTGGC | ACGGCAACGA | 2100 |
| AGTGCCGTAT | GTTTTTGACA | CGTTAAGTCT | GACGCCACCC | GCAAGTGAAT | 2150 |
| ACGTCAACCA | AAACGATCTC | ACGTTTGCCG | GGCAAATTTG | TGACTACTGG | 2200 |
| ACCCGTTTTG | CCCGCAGCGC | CGGTCCCCAC | AGTAAAGCGA | TACCGGGCCG | 2250 |
| GCTAAGCTGG | CCTGCCTGCG | TTCGCGGCAA | GGACCGAACG | ATGCGGTTAG | 2300 |
| GCGTTCACTC | GCGGGCGCGG | TTCAAAGTGG | AAAACCGCTT | TATGCGCATG | 2350 |
| AGAATGCAGC | TGTTTAAGCG | GGTCATGAAG | CATCACGTCA | GCCTTGACTG | 2400 |

*Figure 1B*

Nucleotide sequence of inserted environmental DNA in clone ELIP
(SEQ ID NO:1)

| | | | | | |
|---|---|---|---|---|---|
| AGCAACTCAT | GGCAAAATGC | TTCAAGCCCG | GCGGCGTGCT | CGCTGCCGGG | 2450 |
| TTTAACCGCC | AGACGGTAGC | CCGCACCGGT | TTTTACACTG | CGATCAAACG | 2500 |
| GCCTGACCAG | CCGCCCGGTA | CGAATATCTT | CTGCCACCAG | CGTTTCATCG | 2550 |
| GCGATGGCGA | TCCCAAACCC | CTGAATAGCG | GCGCTGATGG | CGAGATCCAT | 2600 |
| AGTGTCAAAA | TGCTGATTTT | TACTCATTGC | CTGCCAGGGC | GCAAGAAAAC | 2650 |
| CCGGTTCTGC | CAGAAGTGAC | CAGTCGGTGC | GGTCCCGCGT | TGGGTGCAAA | 2700 |
| AATGTCAGTC | TTTCCCAGCC | GCTATCTTCT | TTTGGCAGCA | GGCTCTGGCT | 2750 |
| TACAACCGGC | GTCAGCGCCT | CCTCGAACAA | CAGCGTGCCG | GTTTCGCCG | 2800 |
| ACTGCCCAAA | AACAATTGCC | GCGTCAAACG | GCTCATTTTT | GAAGTTCACG | 2850 |
| CCGTGCTCAA | CGGTCGTGGT | CAGCGCAACC | TGTAGCTCCG | GCATGCGTTG | 2900 |
| TTCAAGCTGA | ATCAGCTTTG | GCACCAGCCA | GCGCATCGCG | CAGGTTGGCG | 2950 |
| CTTTAAGACG | AATAATTTCT | GGCTTGTGGC | AGGCGCGGTC | GGCTACGTCC | 3000 |
| AGCAGATTAT | TGAACGCGCT | TTGTAATTCC | GGGGAGCAGGG | CGCTGCCCTG | 3050 |
| TGGCGTAAGG | CGCAGCCCGC | GCGCGTGGCG | TTCAAAAAGC | GCAAAGCCAA | 3100 |
| GCCACTGTTC | GAGGGCGGCA | ATTTTGCGGC | TGACGGCGCC | CTGGGTGAGG | 3150 |
| CAAAGTTCCT | TCGCGGCCCT | GGTCAGGTTC | AGGTGCCTGG | CGGGTGACGA | 3200 |
| GAAAAGCGTC | CAGAGTATTC | AGGGGAAAAT | TGCGCCGCGT | CATGATGCTC | 3250 |
| TCCGTTGAGC | TATGCATTTT | TTGCATGGCT | ATTATGACAA | CAATTCGATT | 3300 |
| GTCGTGGCAA | TCGCATCCGG | ATTGAATAGT | TATGCAAATC | GCATATTGTT | 3350 |
| CAGGAGCGGC | TATGGCCATG | CAAACCCCGG | TGCAACATCG | TTCAAAACTG | 3400 |
| CCGGATGTAG | GAACCACCAT | ATTTACGGTT | ATCGGTCAGC | TTTCCGCCCA | 3450 |
| ACATAAGGCG | ATCAACCTTT | CTCAGGGCGC | GCCCAACTTC | CCCTGTGACC | 3500 |
| CGCAGCTTAT | TGCCGGAGTC | ACCAGGGCAA | TGCAGGAGGG | GCATAACCAG | 3550 |
| TATGCGTCCA | TGACCGGACT | TGCGTCGCTG | AAAAATCTTA | TTGCTGAAAA | 3600 |
| AGTCGCGGCG | CTTTACGGCT | CAACCTACGA | TCCGGCGGAT | GAAGTGCTGG | 3650 |
| TTACCGCCAG | CGCCAGCGAA | GGGCTGTATT | CCGCTATCGG | CGGACTGGTA | 3700 |
| CACCCCGGCG | ACGAAGTTAT | CTATTTCGAA | CCCTCTTTTG | ACAGCTACGC | 3750 |
| GCCGATTGTT | CGGCTCCAGG | GCGCAACGCC | GGTTGCCCTT | AAGCTCAGCC | 3800 |
| TGCCTGACTT | CACCATTAAC | TGGGATGAAG | TGCGCGCTGC | CATAACGCCG | 3850 |
| CGTACCCGCA | TGATTATTGT | CAACACGCCG | CATAACCCAA | GCGGGCAGGT | 3900 |
| GTTCAGCGCT | CATGATCTCG | AAATGCTGGC | GGCGCTTACC | CGTAATACGG | 3950 |
| ATATCGTTGT | CCTGTCTGAC | GAAGTGTACG | AGCACATCGT | GTTTGACGGA | 4000 |
| CAAAAGCATC | ACGGCATGGC | CACGCACCCG | CAGCTTGCCG | AGCGTAGCGT | 4050 |
| TATCGTTTCA | TCGTTTGGCA | AAACCTTCCA | TGTTACCGGC | TGGCGCGTGG | 4100 |
| GGTACTGCCT | GGCGCCCGCC | GCGTTGATGG | ATGAGATTTG | CAAGGTGCAT | 4150 |
| CAGTTCCTGA | TGTTTTCAGC | CGATACGCCA | ATGCAGCACG | CTTTTGCTGA | 4200 |
| TTACATGAGC | GATCCGCAAA | CTTATCTCTC | GCTGGCGAGC | CTTTACCAGC | 4250 |
| GCAAGCGTGA | TTTAATGCAG | TCTCTGCTGG | CGGAGTCGCC | ATTCGAGCTG | 4300 |
| CTGCCGAGCG | CCG | | | | 4313 |

*Figure 2*

**Nucleotide sequence of ORF for esterase/lipase in ELIP clone
(SEQ ID NO:2)**

| | | | | | |
|---|---|---|---|---|---|
| ATGGTCTGGC | TGCACGGTGG | GGGCTACACT | ATCGGCGCAG | GCTCGCTGCC | 50 |
| GCCCTACGAT | GGAGCAGCCT | TCGCCTCGCG | GGATGTAGTC | CTGGTGACGG | 100 |
| TGAATTACCG | TCTTGGCCAT | CTCGGCTTTT | TCGCCCATCC | GGCGCTGGAT | 150 |
| GAAGAAAATC | CAGACGGCCC | GGTTCATAAT | TTCGCGCTTT | TAGACCAAAT | 200 |
| TGCTGCCCTG | AAATGGGTGC | AGGAAAATAT | CGCTGCTTTC | GGCGGCGACG | 250 |
| CGGGGAATGT | CACGCTGTTT | GGCGAGTCTG | CCGGGGCGCG | TAGCGTGCTT | 300 |
| TCGCTGCTGG | CGTCGCCGCT | GGCGAAAAAC | CTTTTCCACA | AAGGTATTAT | 350 |
| ACAAAGCGCC | TACACGTTGC | CGGATGTCGA | CAGGAAGAAA | GCCCTGAAAC | 400 |
| GTGGCGTAGC | GCTGGCCGGT | CATTACGGGC | TGCAAAATGC | CACAGCGGAT | 450 |
| GAACTCCGCG | CTCTGCCTGC | GGATGGGCTG | TGGGCGCTTG | AAGGGCCGCT | 500 |
| TAACATTGGT | CCAACGCCAA | TCTCCGGCGA | CGTCGTGCTG | CCTGAGCCGA | 550 |
| TGCTGGATAT | ATTCTTCGCC | GGGCGTCAGC | ACCGCATGCC | CTTGATGGTC | 600 |
| GGGAGCAACA | GCGACGAGGC | AAGCGTGCTG | AGCTACTTCG | GCATCGATCC | 650 |
| TGCCGGGCAG | GTCGAACTGC | TGCGCCGGGG | AGCGGCGTTT | CCGGACTGGG | 700 |
| GGCTTATCAA | ACTGCTGTAT | TCCCGGAGTG | AAANGGGGAT | GCCCGAACTC | 750 |
| GGGCGACAGG | TGTGCCGCGA | TATGGCTTTT | NCCNCGCTGG | GTTTTGTTGT | 800 |
| GATGCAGGCC | CAGCAGCGGG | TCAATCAGCC | CTGCTGGCGC | TACTATTTTG | 850 |
| ATTATGTGGG | GGAGGCGGAA | CGTAAAATCT | ATGCCAACGG | CACCTGGCAC | 900 |
| GGCAACGAAG | TGCCGTATGT | TTTTGACACG | TTAAGTCTGA | CGCCACCCGC | 950 |
| AAGTGAATAC | GTCAACCAAA | ACGATCTCAC | GTTTGCCGGG | CAAATTTGTG | 1000 |
| ACTACTGGAC | CCGTTTTGCC | CGCAGCGCCG | GTCCCCACAG | TAAAGCGATA | 1050 |
| CCGGGCCCGC | TAAGCTGGCC | TGCCTGCGTT | CGCGGCAAGG | ACCGAACGAT | 1100 |
| GCGGTTAGGC | GTTCACTCGC | GGGCGCGGTT | CAAAGTGGAA | AACCGCTTTA | 1150 |
| TGCGCATGAG | AATGCAGCTG | TTTAAGCGGG | TCATGAAGCA | TCACGTCAGC | 1200 |
| CTTGACTGA | | | | | 1209 |

*Figure 3*

Translated amino acid sequence of the putative esterase/lipase from the ELIP clone (SEQ ID NO:3)

| | | | | | |
|---|---|---|---|---|---|
| MVWLHGGGYT | IGAGSLPPYD | GAAFASRDVV | LVTVNYRLGH | LGFFAHPALD | 50 |
| EENPDGPVHN | FALLDQIAAL | KWVQENIAAF | GGDAGNVTLF | GESAGARSVL | 100 |
| SLLASPLAKN | LFHKGIIQSA | YTLPDVDRKK | ALKRGVALAG | HYGLQNATAD | 150 |
| ELRALPADGL | WALEGPLNIG | PTPISGDVVL | PEPMLDIFFA | GRQHRMPLMV | 200 |
| GSNSDEASVL | SYFGIDPAGQ | VELLRRGAAF | PDWGLIKLLY | SRSEXGMPEL | 250 |
| GRQVCRDMAF | XXLGFVVMQA | QQRVNQPCWR | YYFDYVGEAE | RKIYANGTWH | 300 |
| GNEVPYVFDT | LSLTPPASEY | VNQNDLTFAG | QICDYWTRFA | RSAGPHSKAI | 350 |
| PGPLSWPACV | RGKDRTMRLG | VHSRARFKVE | NRFMRMRMQL | FKRVMKHHVS | 400 |
| LD* | | | | | 402 |

*Figure 4*
Details of the putative ORF's encoding esterase/lipase activity
| Clone | ORF | | Length | Translated protein |
|---|---|---|---|---|
| | Start position | End position | | |
| ELIP | 1193 | 2401 | 1209 bp | 402 amino acids |
| 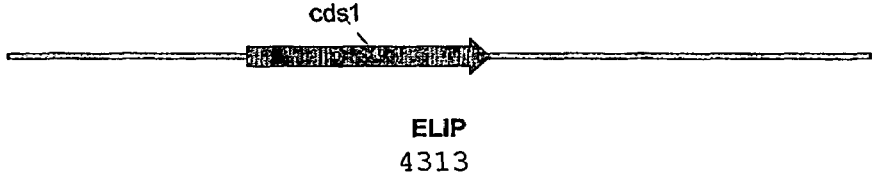 ELIP 4313 ||||
| LIP1 | 1143 | 1934 | 792 bp | 263 amino acids |
| 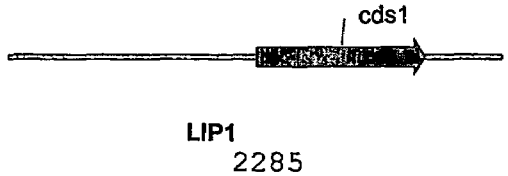 LIP1 2285 ||||
| LIP2 | 2675 | 2031 | 645 bp | 214 amino acids |
|  LIP2 3112 ||||

SEQUENCE LISTING

```
<160> NUMBER OF SEQ ID NOS: 5

<210> SEQ ID NO 1
<211> LENGTH: 4313
<212> TYPE: DNA
<213> ORGANISM: Unknown
<220> FEATURE:
<223> OTHER INFORMATION: uncultured bacterium isolated from Lake
      Elementeita, Kenya
<220> FEATURE:
<221> NAME/KEY: misc_feature
<222> LOCATION: (1926)..(1926)
<223> OTHER INFORMATION: n is a, c, g, or t
<220> FEATURE:
<221> NAME/KEY: misc_feature
<222> LOCATION: (1973)..(1973)
<223> OTHER INFORMATION: n is a, c, g, or t
<220> FEATURE:
<221> NAME/KEY: misc_feature
```

<222> LOCATION: (1976)..(1976)
<223> OTHER INFORMATION: n is a, c, g, or t

<400> SEQUENCE: 1

| | | | | | |
|---|---|---|---|---|---|
| tctatgagca | acaaggcggt | tttagcgaag | cgcaggccga | tgagtttgtg | gccgaggcgc | 60 |
| tggaaacatt | ccgctggcac | cagcacgcaa | cggttgacgc | cgaaacctac | cgcgcgttgc | 120 |
| atgatgagca | ccggctgatc | gccgatgtag | tctgcttccg | tggctgccac | attaaccacc | 180 |
| tgaccccgcg | cacgctcgat | atcgaccgcg | tgcagtcgct | gatgccggaa | cgcggaatta | 240 |
| ccccaaaagc | cattatcgaa | gggccgccgc | gccgcgagcg | cccgatttta | ctgcgccaga | 300 |
| ccagctttaa | agcgctggaa | gagcctattt | tgttcgccgg | tgagcatcac | ggaacgcata | 360 |
| ccgcccgttt | cggcgaaata | gaacagcgcg | gcgtagcgct | gacgccgaaa | ggccgggcgc | 420 |
| tgtacgacga | actgctgctg | gcggcgggca | acggcacgga | taatctcagc | caccagcagc | 480 |
| atttacacga | agtgttcacc | gtttcccgga | cagcgacgcg | ctgctgcgcc | gccaggggct | 540 |
| ggcctatttc | cgctatcgtt | tgacgcccgt | tggcgaaatg | caccgccact | caatcaagcc | 600 |
| aggcgacgac | ccgcagctgc | ttatagaacg | cggctggctg | gtggcgcagc | cggttattta | 660 |
| tgaagatttc | ctcccggtca | gcgcggcggg | tattttccag | tcaaaccttg | gcagcgacgg | 720 |
| cgggcaacgg | cagcacggcc | attccagccg | cagcgagttt | gaacaggccc | ttggcgcaga | 780 |
| ggttgcagac | gagttcgccc | tctatcagca | ggccgaggat | cgcagtaaac | gccgttgcgg | 840 |
| tttgctgtaa | acgcgctacc | ctgctggagt | gtcagtaaca | aggaacagca | gatgaacaa | 900 |
| gttgttagcc | gttgctcagg | ggagactgag | cggcgttctt | caggggaaag | ttgcggtcta | 960 |
| tcgcggcatc | cccttttgccg | ctccgccggt | gggtgaactg | cgctggcggg | cacctcgtcc | 1020 |
| cccggcgcac | tggcagggta | tccgccaggc | ggatacattt | gcgcctgcat | gctggcaaag | 1080 |
| cctcgaatac | tgcaaagcgg | ttggcggcgg | cgatcccggc | cagttttctg | aagattgcct | 1140 |
| gtatctcaat | atctggaccc | cggccgcgcg | ggatgcggag | ccgctgccgg | ttatggtctg | 1200 |
| gctgcacggt | gggggctaca | ctatcggcgc | aggctcgctg | ccgccctacg | atggagcagc | 1260 |
| cttcgcctcg | cgggatgtag | tcctggtgac | ggtgaattac | cgtcttggcc | atctcggctt | 1320 |
| tttcgcccat | ccggcgctgg | atgaagaaaa | tccagacggc | ccggttcata | atttcgcgct | 1380 |
| tttagaccaa | attgctgccc | tgaaatgggt | gcaggaaaat | atcgctgctt | tcggcggcga | 1440 |
| cgcggggaat | gtcacgctgt | ttggcgagtc | tgccgggggcg | cgtagcgtgc | tttcgctgct | 1500 |
| ggcgtcgccg | ctggcgaaaa | accttttcca | caaaggtatt | atacaaagcg | cctacacgtt | 1560 |
| gccggatgtc | gacaggaaga | aagccctgaa | acgtggcgta | gcgctggccg | gtcattacgg | 1620 |
| gctgcaaaat | gccacagcgg | atgaactccg | cgctctgcct | gcggatgggc | tgtgggcgct | 1680 |
| tgaagggccg | cttaacattg | gtccaacgcc | aatctccggc | gacgtcgtgc | tgcctgagcc | 1740 |
| gatgctggat | atattcttcg | ccgggcgtca | gcaccgcatg | cccttgatgg | tcgggagcaa | 1800 |
| cagcgacgag | gcaagcgtgc | tgagctactt | cggcatcgat | cctgccgggc | aggtcgaact | 1860 |
| gctgcgccgg | ggagcggcgt | tccggactg | ggggcttatc | aaactgctgt | attcccggag | 1920 |
| tgaaangggg | atgcccgaac | tcgggcgaca | ggtgtgccgc | gatatggctt | ttnccncgct | 1980 |
| gggttttgtt | gtgatgcagg | cccagcagcg | ggtcaatcag | ccctgctggc | gctactattt | 2040 |
| tgattatgtg | ggggaggcgg | aacgtaaaat | ctatgccaac | ggcacctggc | acggcaacga | 2100 |
| agtgccgtat | gttttttgaca | cgttaagtct | gacgccaccc | gcaagtgaat | acgtcaacca | 2160 |
| aaacgatctc | acgtttgccg | ggcaaatttg | tgactactgg | acccgttttg | cccgcagcgc | 2220 |

```
cggtccccac agtaaagcga taccgggccc gctaagctgg cctgcctgcg ttcgcggcaa    2280
ggaccgaacg atgcggttag gcgttcactc gcgggcgcgg ttcaaagtgg aaaaccgctt    2340
tatgcgcatg agaatgcagc tgtttaagcg ggtcatgaag catcacgtca gccttgactg    2400
agcaactcat ggcaaaatgc ttcaagcccg gcggcgtgct cgctgccggg tttaaccgcc    2460
agacggtagc ccgcaccggt ttttacactg cgatcaaacg gcctgaccag ccgcccggta    2520
cgaatatctt ctgccaccag cgtttcatcg gcgatggcga tcccaaaccc ctgaatagcg    2580
gcgctgatgg cgagatccat agtgtcaaaa tgctgatttt tactcattgc ctgccagggc    2640
gcaagaaaac ccggttctgc cagaagtgac cagtcggtgc ggtcccgcgt tgggtgcaaa    2700
aatgtcagtc tttcccagcc gctatcttct tttggcagca ggctctggct tacaaccggc    2760
gtcagcgcct cctcgaacaa cagcgtgccg gttttcgccg actgcccaaa aacaattgcc    2820
gcgtcaaacg gctcattttt gaagttcacg ccgtgctcaa cggtcgtggt cagcgcaacc    2880
tgtagctccg gcatgcgttg ttcaagctga atcagctttg gcaccagcca gcgcatcgcg    2940
caggttggcg cttaagacg aataatttct ggcttgtggc aggcgcggtc ggctacgtcc    3000
agcagattat tgaacgcgct ttgtaattcc gggagcaggg cgctgccctg tggcgtaagg    3060
cgcagcccgc gcgcgtggcg ttcaaaaagc gcaaagccaa gccactgttc gagggcggca    3120
attttgcggc tgacgcgcc ctgggtgagg caaagttcct tcgcggccct ggtcaggttc    3180
aggtgcctgg cgggtgacga aaaagcgtc cagagtattc aggggaaaat tgcgccgcgt    3240
catgatgctc tccgttgagc tatgcatttt ttgcatggct attatgacaa caattcgatt    3300
gtcgtggcaa tcgcatccgg attgaatagt tatgcaaatc gcatattgtt caggagcggc    3360
tatgccatg caaaccccgg tgcaacatcg ttcaaaactg ccggatgtag gaaccaccat    3420
atttacggtt atcggtcagc tttccgccca acataaggcg atcaaccttt ctcagggcgc    3480
gcccaacttc ccctgtgacc cgcagcttat tgccggagtc accagggcaa tgcaggaggg    3540
gcataaccag tatgcgtcca tgaccggact tgcgtcgctg aaaaatctta ttgctgaaaa    3600
agtcgcggcg ctttacggct caacctacga tccggcggat gaagtgctgg ttaccgccag    3660
cgccagcgaa gggctgtatt ccgctatcgg cggactggta caccccggcg acgaagttat    3720
ctatttcgaa ccctctttg acagctacgc gccgattgtt cggctccagg gcgcaacgcc    3780
ggttgccctt aagctcagcc tgcctgactt caccattaac tgggatgaag tgcgcgctgc    3840
cataacgccg cgtacccgca tgattattgt caacacgccg cataacccaa gcgggcaggt    3900
gttcagcgct catgatctcg aaatgctggc ggcgcttacc cgtaatacgg atatcgttgt    3960
cctgtctgac gaagtgtacg agcacatcgt gtttgacgga caaaagcatc acggcatggc    4020
cacgcacccg cagcttgccg agcgtagcgt tatcgtttca tcgtttggca aaaaccttcca   4080
tgttaccggc tggcgcgtgg ggtactgcct ggcgcccgcc gcgttgatgg atgagatttg    4140
caaggtgcat cagttcctga tgttttcagc cgatacgcca atgcagcacg cttttgctga    4200
ttacatgagc gatccgcaaa cttatctctc gctggcgagc ctttaccagc gcaagcgtga    4260
tttaatgcag tctctgctgg cggagtcgcc attcgagctg ctgccgagcg ccg           4313
```

<210> SEQ ID NO 2
<211> LENGTH: 1209
<212> TYPE: DNA
<213> ORGANISM: Unknown
<220> FEATURE:
<223> OTHER INFORMATION: uncultured bacterium isolated from Lake
      Elementeita, Kenya
<220> FEATURE:

<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t

<400> SEQUENCE: 2

```
atggtctggc tgcacggtgg gggctacact atcggcgcag gctcgctgcc gccctacgat     60
ggagcagcct tcgcctcgcg ggatgtagtc ctggtgacgg tgaattaccg tcttggccat    120
ctcggctttt tcgcccatcc ggcgctggat gaagaaaatc cagacggccc ggttcataat    180
ttcgcgcttt tagaccaaat tgctgccctg aaatgggtgc aggaaaatat cgctgctttc    240
ggcggcgacg cggggaatgt cacgctgttt ggcgagtctg ccggggcgcg tagcgtgctt    300
tcgctgctgg cgtcgccgct ggcgaaaaac cttttccaca aaggtattat acaaagcgcc    360
tacacgttgc cggatgtcga caggaagaaa gccctgaaac gtggcgtagc gctggccggt    420
cattacgggc tgcaaaatgc cacagcggat gaactccgcg ctctgcctgc ggatgggctg    480
tgggcgcttg aagggccgct taacattggt ccaacgccaa tctccggcga cgtcgtgctg    540
cctgagccga tgctggatat attcttcgcc gggcgtcagc accgcatgcc cttgatggtc    600
gggagcaaca gcgacgaggc aagcgtgctg agctacttcg catcgatcc tgccgggcag     660
gtcgaactgc tgcgccgggg agcggcgttt ccggactggg ggcttatcaa actgctgtat    720
tcccggagtg aaangggat gcccgaactc gggcgacagg tgtgccgcga tatggctttt    780
nccncgctgg gttttgttgt gatgcaggcc cagcagcggg tcaatcagcc ctgctggcgc    840
tactattttg attatgtggg ggaggcggaa cgtaaaatct atgccaacgg cacctggcac    900
ggcaacgaag tgccgtatgt ttttgacacg ttaagtctga cgccaccgc aagtgaatac      960
gtcaaccaaa cgatctcac gtttgccggg caaatttgtg actactggac ccgttttgcc    1020
cgcagcgccg gtccccacag taaagcgata ccgggcccgc taagctggcc tgcctgcgtt   1080
cgcggcaagg accgaacgat gcggttaggc gttcactcgc gggcgcggtt caaagtggaa    1140
aaccgcttta tgcgcatgag aatgcagctg tttaagcggg tcatgaagca tcacgtcagc    1200
cttgactga                                                           1209
```

<210> SEQ ID NO 3
<211> LENGTH: 402
<212> TYPE: PRT
<213> ORGANISM: Unknown
<220> FEATURE:
<223> OTHER INFORMATION: uncultured bacterium isolated from Lake Elementeita, Kenya
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (261)..(262)
<223> OTHER INFORMATION: Xaa can be any naturally occurring amino acid

<400> SEQUENCE: 3

```
Met Val Trp Leu His Gly Gly Gly Tyr Thr Ile Gly Ala Gly Ser Leu
1               5                   10                  15

Pro Pro Tyr Asp Gly Ala Ala Phe Ala Ser Arg Asp Val Val Leu Val
```

```
                    20                  25                  30
Thr Val Asn Tyr Arg Leu Gly His Leu Gly Phe Phe Ala His Pro Ala
            35                  40                  45
Leu Asp Glu Glu Asn Pro Asp Gly Pro Val His Asn Phe Ala Leu Leu
        50                  55                  60
Asp Gln Ile Ala Ala Leu Lys Trp Val Gln Glu Asn Ile Ala Ala Phe
65                  70                  75                  80
Gly Gly Asp Ala Gly Asn Val Thr Leu Phe Gly Glu Ser Ala Gly Ala
                    85                  90                  95
Arg Ser Val Leu Ser Leu Leu Ala Ser Pro Leu Ala Lys Asn Leu Phe
                100                 105                 110
His Lys Gly Ile Ile Gln Ser Ala Tyr Thr Leu Pro Asp Val Asp Arg
            115                 120                 125
Lys Lys Ala Leu Lys Arg Gly Val Ala Leu Ala Gly His Tyr Gly Leu
        130                 135                 140
Gln Asn Ala Thr Ala Asp Glu Leu Arg Ala Leu Pro Ala Asp Gly Leu
145                 150                 155                 160
Trp Ala Leu Glu Gly Pro Leu Asn Ile Gly Pro Thr Pro Ile Ser Gly
                    165                 170                 175
Asp Val Val Leu Pro Glu Pro Met Leu Asp Ile Phe Phe Ala Gly Arg
                180                 185                 190
Gln His Arg Met Pro Leu Met Val Gly Ser Asn Ser Asp Glu Ala Ser
            195                 200                 205
Val Leu Ser Tyr Phe Gly Ile Asp Pro Ala Gly Gln Val Glu Leu Leu
        210                 215                 220
Arg Arg Gly Ala Ala Phe Pro Asp Trp Gly Leu Ile Lys Leu Leu Tyr
225                 230                 235                 240
Ser Arg Ser Glu Xaa Gly Met Pro Glu Leu Gly Arg Gln Val Cys Arg
                    245                 250                 255
Asp Met Ala Phe Xaa Xaa Leu Gly Phe Val Val Met Gln Ala Gln Gln
                260                 265                 270
Arg Val Asn Gln Pro Cys Trp Arg Tyr Tyr Phe Asp Tyr Val Gly Glu
            275                 280                 285
Ala Glu Arg Lys Ile Tyr Ala Asn Gly Thr Trp His Gly Asn Glu Val
        290                 295                 300
Pro Tyr Val Phe Asp Thr Leu Ser Leu Thr Pro Ala Ser Glu Tyr
305                 310                 315                 320
Val Asn Gln Asn Asp Leu Thr Phe Ala Gly Gln Ile Cys Asp Tyr Trp
                    325                 330                 335
Thr Arg Phe Ala Arg Ser Ala Gly Pro His Ser Lys Ala Ile Pro Gly
                340                 345                 350
Pro Leu Ser Trp Pro Ala Cys Val Arg Gly Lys Asp Arg Thr Met Arg
            355                 360                 365
Leu Gly Val His Ser Arg Ala Arg Phe Lys Val Glu Asn Arg Phe Met
        370                 375                 380
Arg Met Arg Met Gln Leu Phe Lys Arg Val Met Lys His His Val Ser
385                 390                 395                 400
Leu Asp

<210> SEQ ID NO 4
<211> LENGTH: 16
<212> TYPE: PRT
<213> ORGANISM: Unknown
<220> FEATURE:
```

```
<223> OTHER INFORMATION: uncultured bacterium isolated from Lake
      Elementeita, Kenya

<400> SEQUENCE: 4

Phe Gly Gly Asp Ala Gly Asn Val Thr Leu Phe Gly Glu Ser Ala Gly
1               5                   10                  15

<210> SEQ ID NO 5
<211> LENGTH: 16
<212> TYPE: PRT
<213> ORGANISM: Artificial
<220> FEATURE:
<223> OTHER INFORMATION: synthetic characteristic sequence motif
      construct
<220> FEATURE:
<221> NAME/KEY: misc_feature
<222> LOCATION: (2)..(2)
<223> OTHER INFORMATION: Xaa can be Gly or Arg
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Leu, Ile, Val or Met
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be Leu, Ile or Val
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be Ser, Thr, Ala or Gly

<400> SEQUENCE: 5

Phe Xaa Gly Xaa Xaa Xaa Xaa Xaa Xaa Xaa Xaa Gly Xaa Ser Xaa Gly
1               5                   10                  15
```

US 7,511,005 B2

LIPOLYTIC ENZYME ELIP

This application is a national stage entry of PCT/US04/14685, filed May 12, 2004, which claims priority to provisional application 60/470,069, filed May 12, 2003.

STATEMENT AS TO RIGHTS TO INVENTIONS MADE UNDER FEDERALLY SPONSORED RESEARCH AND DEVELOPMENT

Not Applicable.

FIELD OF THE INVENTION

The present invention relates to novel lipolytic enzymes and polynucleotides encoding the lipolytic enzyme polypeptides. The invention also relates to nucleic acid constructs, vectors, and host cells comprising the nucleic acid constructs as well as methods for producing and using the polypeptides.

BACKGROUND OF THE INVENTION

For a number of years lipolytic enzymes have been used as detergent enzymes, i.e. to remove lipid or fatty stains from clothes and other textiles.

Lipolytic enzymes include, but are not limited to, lipases and esterases. Lipases are versatile biocatalysts that can perform innumerable different reactions. Unlike other hydrolases that work in aqueous phase, lipases are unique as they act at the oil/water interface. Besides being lipolytic, lipases also possess esterolytic activity and thus have a wide substrate range.

A need exists for novel lipolytic enzymes having improved washing and/or dishwashing properties, and the object of the present invention is to prepare such enzymes Although lipolytic compositions have been previously described, there remains a need for new and improved lipolytic compositions for use in household detergents, or laundry detergents, etc. Lipases that exhibit improved performance are of particular interest.

BRIEF SUMMARY OF THE INVENTION

In a first aspect, the present invention relates to a polypeptide having lipolytic activity, designated herein as ELIP. In some embodiments, the present invention relates to a substantially pure polypeptide or lipolytic enzyme having lipolytic activity, wherein said polypeptide or lipolytic enzyme comprises an amino acid sequence having at least 75%, at least 85%, at least 95% amino acid sequence identity with an amino acid sequence set forth in SEQ ID NO.:3, wherein said polypeptide has lipolytic activity. In other embodiments, the polypeptide comprises an amino acid sequence having at least 75% sequence identity with an ELIP amino acid sequence set forth in SEQ ID NO.:3 and is encoded by a polynucleotide having a nucleic acid sequence having at least 75%, at least 85%, or at least 95% nucleic acid sequence identity with a nucleic acid sequence set forth in SEQ ID NO.:1. In another embodiment, the polynucleotide or lipolytic enzyme is derived from *Bacillus*. In another embodiment, the polynucleotide encoding a lipolytic enzyme is shown in FIG. 3.

In second aspect the present invention relates to a polynucleotide encoding a lipolytic polypeptide or enzyme. In one embodiment, the polynucleotide encodes a lipolytic polypeptide or enzyme is derived from *Bacillus*. In other embodiments, the polynucleotide encodes an amino acid sequence having at least 75% sequence identity with an ELIP amino acid sequence set forth in SEQ ID NO.:3 and has a nucleic acid sequence having at least 75%, at least 85%, or at least 95% nucleic acid sequence identity with a nucleic acid sequence set forth in SEQ ID NO.:1. In another embodiment, the polynucleotide encodes a lipolytic polypeptide or enzyme having an amino acid sequence shown in FIG. 3.

In a third aspect the present invention relates to a nucleic acid construct comprising the nucleotide sequence, which encodes for an inventive lipolytic polypeptide or enzyme, operably linked to one or more control sequences that direct the production of the lipolytic polynucleotide or enzyme in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a lipolytic enzyme of the invention, the method comprising
 a) transforming a host cell with a nucleic acid encoding an inventive lipolytic polynucleotide or enzyme described herein;
 b) culturing the host cell under conditions to produce the polypeptide or enzyme; and
 c) recovering the polypeptide or enzyme.

BRIEF DESCRIPTION OF THE DRAWINGS

FIG. 1 is the genomic DNA sequence for ELIP (SEQ ID NO:1). The coding sequence is in bold and underlined.

FIG. 2 is the cDNA sequence for ELIP (SEQ ID NO:2).

FIG. 3 is the amino acid sequence for ELIP (SEQ ID NO:3).

FIG. 4 is a table summarizing the details of the putative ORF's encoding the inventive proteins with esterase/lipase activity.

DETAILED DESCRIPTION

The invention will now be described in detail by way of reference only using the following definitions and examples. All patents, patent applications, articles and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

The terms "lipolytic polypeptides", "lipolytic proteins", "lipolytic enzymes" or "lipase enzymes" refer to a polypeptide, protein or enzyme exhibiting a lipid degrading capability such as a capability of degrading a triglyceride or a phospholipid. The lipolytic enzyme may be, for example, a lipase, a phospholipase, an esterase or a cutinase. The phrase "esterase/lipase enzyme" may be used interchangeably herein.

For the present invention, lipolytic activity may be determined according to any procedure known in the art. See, for example, Gupta et al, Biotechnol. Appl. Biochem. (2003) 37:63-71; Andre, Christophe, et al, U.S. Pat. No. 5,990,069 (International Publication WO 96/18729A1).

The term "% homology" is used interchangeably herein with the term "% identity" herein and refers to the level of nucleic acid or amino acid sequence identity between the nucleic acid sequence that encodes a lipolytic polypeptide, lipolytic enzyme, lipase enzyme or the lipase amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 50, 55, 60, 65, 70, 75, 80, 85, 90, 93, 95, 97, 98 and 99% or more sequence identity to a given sequence, e.g., the coding sequence for ELIP, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997).

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The term "derived" encompasses the terms originated from, obtained or obtainable from, and isolated from.

The term "nucleic acid" refers to DNA, RNA, single stranded or double stranded and chemical modifications thereof. The terms "nucleic acid", "polynucleotide" or "nucleic acid molecule" may be used interchangeably herein. Because the genetic code is degenerate, more than one codon may be used to encode a particular amino acid, and the present invention.

The term "protein" refers to polymers of large molecular mass composed of one or more polypeptide chains and whose monomers are amino acids joined together by peptide bonds. The terms "protein" and "polypeptide" are sometimes used interchangeably herein. The conventional one-letter or three-letter code for amino acid residues is used herein.

The term "enzyme" refers to a protein having catalytic activity. For example, catalytic activity includes lipolytic activity. The conventional one-letter or three-letter code for amino acid residues is used herein.

The term "host cell" refers to a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In a one embodiment according to the present invention, "host cell" means the cells of the genus *Bacillus*. In another preferred embodiment according to the invention, "host cell" means the cells of *Streptomyces*. A *Streptomyces* means any bacterial strain that is a member of the genus *Streptomyces* as classified in Buchanan et al., *The Shorter Bergey's Manual For Determinative Bacteriology* (Williams & Wilkens 1982). Particularly preferred strains of *Streptomyces* include *S. lividens, S. rubiginosus,* and *S. coelicolor. S. lividens* is described in Lomovskaya et al., *J. Virology* 9:258 (1972). However, one of skill will realize that any appropriate host cell, e.g., bacterial, fungal, eukaryotic and plant cell may be used.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. Also encompassed by the present invention is the overexpression of a native gene, possibility due to the presence of additional copies of a native gene, or associating a native gene with a promoter that is heterologous to the gene.

The term "secretory signal sequence" refers to a DNA sequence that encodes a polypeptide (a "secretory peptide" or "secretory signal peptide") that, as a component of a larger polypeptide, directs the larger polypeptide through a secretory pathway of a cell in which it is synthesized. The larger peptide is commonly cleaved to remove the secretory peptide during transit through the secretory pathway to yield the secretory signal peptide and a smaller peptide commonly referred to as the mature polypeptide.

A "naturally occurring" composition is one produced by a naturally occurring source and which comprises one or more of the inventive lipolytic or lipase components wherein each of these components is found in a proportion relative to other proteins produced by the source. A naturally occurring composition is one that is produced by an organism unmodified with respect to the lipase enzymes such that the ratio of the component enzymes is unaltered from that produced by the native organism.

A "non-naturally occurring" composition encompasses those compositions produced by: (1) combining component lipase polypeptides or enzymes either in a naturally occurring ratio or non-naturally occurring, i.e., altered, ratio; or (2) modifying an organism to overexpress or underexpress one or more lipolytic polypeptide or enzyme; or (3) modifying an organism such that at least one lipolytic polypeptide or enzyme is deleted or (4) modifying an organism to express a heterologous component lipolytic polypeptide or enzyme.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. The promoter may be the promoter normally associated with the downstream gene or it may be heterologous, i.e., from another gene or another microorganism as long as it function to direct the gene. Examples of suitable promoters for directing the transcription of the DNA sequence encoding a variant of the invention, especially in a bacterial host, are the promoter of the lac operon of *E. coli,* the *Streptomyces coelicolor* agarase gene dagA promoters, the promoters of the *Bacillus licheniformis* α-amylase gene (amyL), e.g. as described in WO 93/10249 the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. A preferred promoter when the transformation host cell is *Bacillus* is the aprE promoter. In one aspect the promoter is an inducible promoter. In one aspect, when the host cell is a filamentous fungus, the promoter is the *T. reesei* cbh1 promoter which is deposited in GenBank under Accession Number D86235. In another aspect the promoter is a cbh II or xylanase promoter from *T. reesei.*

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "nucleic acid construct", "DNA construct" or "DNA vector" refer to a nucleotide or nucleic acid sequence which comprises one or more DNA fragments encoding the novel lipolytic polypeptide or enzyme. Included in "DNA vectors" are "expression vectors." Typical expression vectors contain regulatory sequences such as, transcription and translation terminators, transcription and translation initiation sequences, signal sequences, and promoters useful for regulation of the expression of the particular nucleic acid. The term "promoter" is used in its ordinary sense to refer to a polynucleotide sequence involved in the control of the initiation of transcription of a polynucleotide sequence encoding a protein. A "signal sequence" refers to a signal peptide or a portion of a protein that is capable of directing the transport of a desired protein in bioactive form from a host. The mature form of an extracellular protein lacks the signal sequence which is cleaved off during the secretion process. While not meant to limit the invention, the number of amino acid residues in a signal peptide may be between about 5 and about 100 amino acid residues. Signal sequence may be modified to provide for cloning sites that allow for the ligation of DNA or insertion of DNA encoding a lipolytic polypeptide or enzyme. The vectors optionally comprise generic expression cassettes containing at least one independent terminator sequence, sequences permitting replication of the cassette in prokaryotes, eukaryotes, or both, (e.g., shuttle vectors) and selection markers for both prokaryotic and eukaryotic systems. Vectors are suitable for replication and integration in prokaryotes, eukaryotes, or both. See, Giliman and Smith, *Gene* 8:81-97 (1979); Roberts et al., *Nature* 328:731-734 (1987); Berger and Kimmel, GUIDE TO MOLECULAR CLONING TECHNIQUES, METHODS IN ENZYMOLOGY, VOL 152, Academic Press, Inc., San Diego, Calif. ("Berger"); Scheider, B., et al., *Protein Expr. Purif* 6435:10 (1995); Sambrook et al. MOLECULAR CLONING-A LABORATORY MANUAL (2ND ED.) VOL. 1-3, Cold Springs Harbor Publishing (1989) ("Sambrook"); and CURRENT PROTOCOLS IN MOLECULAR BIOLOGY, Ausubel et al. (eds.), Current Protocols, a joint venture between Greene Publishing Associates, Inc. and John Wiley & Sons, Inc., (1997 Supplement) ("Ausubel"). Cloning vectors useful in *Streptomyces* are known and reference is made to U.S. Pat. Nos. 4,338,397; 4,411,994; 4,513,085; 4,513,086; 4,745,056; 5,514,590; and 5,622,866 and WO88/07079.

The term "gene" refers to the segment of DNA involved in producing a polypeptide chain or protein, that may or may not include regions preceding and following the coding region, e.g. 5' untranslated (5' UTR) or "leader" sequences and 3' UTR or "trailer" sequences, as well as intervening sequences (introns) between individual coding segments (exons).

The terms "heterologous" or "exogenous" with reference to a polynucleotide or protein refer to a polynucleotide or protein that does not naturally occur in a host cell. In some embodiments, the protein is a commercially important industrial protein. It is intended that the term encompass proteins that are encoded by naturally occurring genes, mutated genes and/or synthetic genes. For example the nucleic acid sequence may comprise two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The terms "homologous" or "endogenous" with reference to a polynucleotide, protein or enzyme refer to a polynucleotide, protein or enzyme that occurs naturally in the host cell.

The terms "isolated" or "purified" refer to a nucleic acid, amino acid or protein that is removed from at least one component with which it is naturally associated.

The term "substantially pure polypeptide", "substantially pure enzyme" refers to a polypeptide or enzyme preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

In general, nucleic acid molecules which encode an inventive lipolytic polypeptide or enzyme will hybridize, under moderate to high stringency conditions to the sequence provided herein as SEQ ID NO:2 (cDNA sequences). However, in some cases a lipase-encoding nucleotide sequence is employed that possesses a substantially different codon usage, while the protein encoded by the lipase-encoding nucleotide sequence has the same or substantially the same amino acid sequence as the native protein. For example, the coding sequence may be modified to facilitate faster expression of an inventive lipase in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The terms "transformed", "stably transformed" or "transgenic" with reference to a cell refers to a cell has a non-native (heterologous) nucleic acid sequence integrated into its genome or as an episomal plasmid that is maintained through multiple generations.

The term "expression" refers to the process by which a polypeptide is produced based on the nucleic acid sequence of a gene. The process includes both transcription and translation.

The term "introduced" in the context of inserting a nucleic acid sequence into a cell, includes "transfection", or "transformation" or "transduction" and refers to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the terms "lipolytic polypeptide expression", "lipolytic enzyme expression" and "lipase expression" refer to transcription and translation of an inventive lipolytic polypeptide, lipolytic enzyme or lipase gene, the products of which include precursor RNA, mRNA, polypeptide, post-translationally processed polypeptides. By way of example, assays for lipase expression include Western blot for a lipase protein, Northern blot analysis and reverse transcriptase polymerase chain reaction (RT-PCR) assays for lipase mRNA, and lipase activity assays as known in the art.

The term "surfactant" refers to any compound generally recognized in the art as having surface active qualities. Thus, for example, surfactants comprise anionic, cationic and non-ionic surfactants such as those commonly found in detergents. Anionic surfactants include linear or branched alkyl-benzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

The term "detergent composition" refers to a mixture which is intended for use in a wash medium for the laundering of soiled fabrics. In the context of the present invention, such compositions may include, in addition to lipases and surfactants, additional enzymes (e.g., hydrolytic, proteolytic, etc.), builders, bleaching agents, bleach activators, bluing agents and fluorescent dyes, caking inhibitors, masking agents, activators, antioxidants, and solubilizers.

The terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

When employed in enzymatic solutions, the inventive lipolytic polypeptide or enzyme component is generally added in an amount sufficient to allow the highest rate of fatty stain removal, which can be readily determined by the skilled artisan. However, when employed, the weight percent of the lipolytic polypeptide or enzyme component is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Molecular Biology I

In one embodiment this invention provides for the expression of lipolytic polypeptide or enzyme genes under the control of a promoter functional in a host cell. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

In one embodiment, the polypeptide having lipolytic activity has at least 50%, 55%, 60%, 65%, 70%, 75%, 80%, 85%, 90%, 93%, 95%, 97%, 98% and 99% sequence identity with the ELIP amino acid sequence set forth in SEQ ID NO: 3. In other embodiments, the polypeptide having lipolytic activity comprises the amino acid sequence of SEQ ID NO: 3

In one embodiment, the polypeptide having lipolytic activity has at least 50%, 55%, 60%, 65%, 70%, 75%, 80%, 85%, 90%, 93%, 95%, 97%, 98% and 99% sequence identity with the ELIP amino acid sequence set forth in SEQ ID NO: 3. In other embodiments, the polypeptide having lipolytic activity comprises the amino acid sequence of SEQ ID NO: 3 or a polypeptide having lipolytic enzyme having at least 80% sequence identity with the sequence of SEQ ID NO: 3 is encoded by a nucleic acid sequence having at least 70%, 80%, 85%, 90%, 93%, 95%, 97%, 98% and 99% nucleotide sequence identity with SEQ ID NO:1.

In one embodiment, the nucleotide sequence encoding a polypeptide having lipolytic activity has at least 50%, 55%, 60%, 65%, 70%, 75%, 80%, 85%, 90%, 93%, 95%, 97%, 98% and 99% sequence identity with the ELIP nucleotide sequence set forth in SEQ ID NO: 1. In other embodiments, the nucleic acid sequence encoding a polypeptide having lipolytic activity comprises the ELIP nucleic acid sequence of SEQ ID NO: 1

A polynucleotide (nucleic acid sequence) or polypeptide (amino acid sequence) having a certain percent (e.g., 50%, 55%, 60%, 65%, 70%, 75%, 80%, 85%, 90%, 93%, 95%, 97%, 98% or 99%) of sequence identity with another sequence means that when aligned, that percent of bases or amino acid residues are the same in comparing the two sequences. This alignment and the percent homology or identity can be determined using any suitable software program known in the art, for example those described in *Current Protocols in Molecular Biology* (Ausubel et al., eds 1987 Supplement 30, section 7.7.18). Preferred programs include GCG Pileup program, FASTA and BLAST. Another preferred alignment program is ALIGN Plus and TFASTA.

In one embodiment, the polynucleotide or polypeptide is derived from *Bacillus*.

A. Methods for Identifying Lipolytic Enzyme Genes

The invention, in one aspect, encompasses a nucleic acid molecule encoding a lipolytic polypeptide or enzyme described herein. The nucleic acid may be a DNA molecule.

Techniques that can be used to isolate lipolytic polypeptide or enzyme-encoding DNA sequences are well known in the art and include, but are not limited to, cDNA and/or genomic library screening with a homologous DNA probes and expression screening with activity assays or antibodies against a lipolytic polypeptide or enzyme. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

The invention, in one aspect, encompasses a nucleic acid molecule encoding a lipolytic polypeptide or enzyme described herein. The nucleic acid may be a DNA molecule.

Techniques that can be used to isolate lipolytic polypeptide or enzyme-encoding DNA sequences are well known in the art and include, but are not limited to, cDNA and/or genomic library screening with a homologous DNA probes and expression screening with activity assays or antibodies against a lipolytic polypeptide or enzyme. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

A genomic library of the collected samples may be prepared using standard techniques known in the art. clones were screened for lipase/esterase activities by plating onto substrate-containing media, to give approximately 1000 colonies per 7 $cm^2$ diameter plate. Positive clones were identified by the faint zone of clearing around them.

Positive clones may then have the plasmid DNA sequenced, including the inserted DNA, using primer sites within the plasmid using standard techniques. Complete coverage of the sequence was obtained by 'primer walking' from both the 5' and 3' ends of the insert. See Kieleczawa et al., Science (1992) 258:1787-91.

The process for isolating a gene according to the second aspect of the present invention makes use of its homology to a nucleotide sequence comprising all or part of the nucleotide sequence of encoding a novel polypeptide or lipolytic enzyme. Examples of such processes include:

a) screening a gene library which presumably contains a lipolytic polypeptide. or enzyme gene using the nucleotide sequence as a probe.

b) preparing a primer based on the nucleotide sequence information, then performing PCR using a sample which presumably contains a lipolytic polypeptide or enzyme gene as a template.

More specifically, process a) above comprises:

a) preparing a gene library which presumably contains a lipolytic polypeptide or enzyme gene, screening the gene library using a nucleotide sequence comprising all or part of the nucleotide sequence of SEQ ID NO:2 as shown in the sequence listing to select sequences which hybridize with the nucleotide sequence comprising all or part of the nucleotide sequence of SEQ ID NO:2 as shown in the sequence listing from the gene library, then isolating the selected sequences, and isolating a ELIP gene from the sequences which have been selected and isolated from the gene library.

The gene library may be a genomic DNA library or a cDNA library, and may be prepared according to a known procedure.

To obtain high level expression of a cloned gene, the heterologous gene is preferably positioned about the same distance from the promoter as is in the naturally occurring lipolytic polypeptide or enzyme gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

B. Nucleic Acid Constructs/Expression Vectors.

Natural or synthetic polynucleotide fragments encoding a novel lipolytic polypeptide or enzyme may be incorporated into heterologous nucleic acid constructs or vectors, capable of introduction into, and replication in, a bacterial, a filamentous fungal or yeast cell. The vectors and methods disclosed herein are suitable for use in host cells for the expression of a lipolytic polypeptide or enzyme. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C.A.M.J.J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. The only constraint on the choice of promoter is that it is functional in the host cell used. A preferred promoter when the transformation host cell is Bacillus is the aprE promoter.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

The methods of transformation of the present invention may result in the stable integration of all or part of the transformation vector into the genome of the host cell. However, transformation resulting in the maintenance of a self-replicating extra-chromosomal transformation vector is also contemplated.

The gene encoding the lipolytic polypeptide or enzyme of the present invention can be cloned using λ-phage (expression) vectors and E. coli host cells. (Alternatively PCR cloning using consensus primers designed on conserved domains may be used.) Applicants have discovered that transformation of the gene encoding the lipolytic polypeptide or enzyme of the present invention and expression in E. coli results in an active protein. After a first cloning step in E. coli, a lipolytic polypeptide or enzyme gene according to the present invention can be transferred to a more preferred industrial expression host such as Bacillus or Streptomyces species, a filamentous fungus such as Aspergillus or Trichoderma, or a yeast such as Saccharomyces. High level expression and secretion obtainable in these host organisms allows accumulation of the lipolytic polypeptide or enzyme in the fermentation medium from which it can subsequently be recovered.

III. Host Organisms

Suitable host organisms may be any microbe useful in industrial settings, such as bacterial, fungi, yeast and the like.

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, Trichoderma, e.g., Trichoderma longibrachiatum, Trichoderma viride, Trichoderma koningii, Trichoderma harzianum; Penicillium sp.; Humicola sp., including Humicola insolens and Humicola grisea; Chrysosporium sp., including C. lucknowense; Gliocladium sp.; Aspergillus sp.; Fusarium sp., Neurospora sp., Hypocrea sp., and Emericella sp. As used herein, the term "Trichoderma" or "Trichoderma sp." refers to any fungal strains which have previously been classified as Trichoderma or are currently classified as Trichoderma.

Examples of parental cell lines which may be treated and/or modified for lipolytic polypeptide or enzyme expression include, but are not limited to, filamentous fungal cells. Examples of appropriate primary cell types for use in practicing the invention include, but are not limited to, Aspergillus and Trichoderma.

In one embodiment, the filamentous fungal parent cell is an Aspergillus niger, Aspergillus awamori, Aspergillus aculeatus, or Aspergillus nidulans cell.

In another embodiment, the filamentous fungal parent cell is a Trichoderma reesei cell.

In a further embodiment, the filamentous fungal parent cell is a Hypocrea jecorina cell. This cell was previously referred to as T. reesei.

In a further embodiment, the host cell is a gram negative Bacteria. In one embodiment, the gram negative Bacteria is *Escherichia coli* ("*E. coli*"). Numerous *E. coli* strains are known, for example JM101 hsdS recA (CBS 155.87); and K12 DH1 (ATCC 33849). In another embodiment, the gram negative Bacteria is *Pseudomonas* sp. In another embodiment, the *Pseudomonas* sp. is *Psuedomonas pseudoalcaligenes*.

In a yet further embodiment, the host cell is a *Bacillus* sp. One type of *Bacillus* strain of interest is a cell of an alkalophilic *Bacillus*. Numerous alkalophilic *Bacillus* strains are known (U.S. Pat. No. 5,217,878 and Aunstrup et al., Proc IV IFS: *Ferment. Technol. Today,* 299-305 (1972)). Another type of *Bacillus* strain of interest is a cell of an industrial *Bacillus* strain. Examples of industrial *Bacillus* strains are *B. licheniformis, B. lentus, B. subtilis,* and *B. amyloliquefaciens*. In another aspect, the *Bacillus* host strain may be *B. licheniformis, B subtilis, B. lentus, B. brevis, B. stearothermophilus, B. alkalophilus, B. amyloliquefaciens, B. coagulans, B. circulans, B. pumilus, B. thuringiensis, B. clausii,* and *B. megaterium*. Particularly preferred are *B. subtilis* cells. U.S. Pat. Nos. 5,264,366 and 4,760,025 (RE 34,606) disclose various *Bacillus* host strains that may be used in accordance with the invention.

An industrial strain may be a non-recombinant strain of a *Bacillus* sp., a mutant of a naturally occurring strain or a recombinant strain. Preferably the host strain is a recombinant host strain wherein a polynucleotide encoding a lipolytic polypeptide or enzyme has been introduced into the host. A further preferred host strain is a *Bacillus subtilis* host strain and particularly a recombinant *Bacillus subtilis* host strain. Numerous *B. subtilis* strains are known, for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100(ATCC 39,094), GX4931, PBT 110, and PEP 211 strain. Hoch et al., (1973) *Genetics,* 73:215-228; U.S. Pat. Nos. 4,450,235; 4,302,544 and EP-A-0134048).

The use of *B. subtilis* as an expression host is disclosed in Palva et al. *Gene* (1982) 19:81-87. Also see Fahnestock and Fischer. *J. Bacteriol.* (1986) 165:796-804; and Wang et al., *Gene* (1988) 69:39-47 for descriptions of heterologous gene expression in *B. subtilis*.

IV. Molecular Biology II

A. Nucleic Acid Constructs/Expression Vectors.

A lipolytic polypeptide or enzyme coding sequence may be inserted into a suitable vector according to well-known recombinant techniques and used to transform host cell capable of lipolytic polypeptide or enzyme expression. Due to the inherent degeneracy of the genetic code, other nucleic acid sequences which encode substantially the same or a functionally equivalent amino acid sequence may be used to clone and express a lipolytic polypeptide or enzyme. Therefore it is appreciated that such substitutions in the coding region fall within the sequence variants covered by the present invention.

The present invention also includes recombinant nucleic acid constructs comprising one or more of the lipolytic polypeptide or enzyme-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a lipolytic polypeptide or enzyme: (i) in isolation; (ii) in combination with additional coding sequences; such as fusion protein or signal peptide coding sequences, where the lipolytic polypeptide or enzyme coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the lipolytic polypeptide or enzyme coding sequence is a heterologous gene.

In one aspect of the present invention, a heterologous nucleic acid construct is employed to transfer a lipolytic polypeptide or enzyme-encoding nucleic acid sequence into a cell in vitro. For long-term, production of a lipolytic polypeptide or enzyme, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

The choice of the proper selectable marker will depend on the host cell, and appropriate markers for different hosts are well known in the art.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991.

B. Methods for Transforming a Host Cell

After DNA sequences that encode the lipolytic polypeptide or enzyme have been cloned into DNA constructs, the DNA is used to transform microorganisms.

Various methods may be employed for delivering an expression vector, DNA vector or construct described above into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; *Agrobacterium*-mediated transfer of DNA; and the like. In addition, heterologous nucleic acid constructs comprising a lipolytic polypeptide or enzyme-encoding nucleic acid sequence can be transcribed in vitro, and the resulting RNA introduced into the host cell by well-known methods, e.g., by injection.

The DNA construct will generally be functionally attached, i.e., operably linked, to a promoter. The transformed host cell is then grown under conditions so as to express the lipolytic polypeptide or enzyme. Subsequently, the lipolytic polypeptide or enzyme may be isolated. It may be desirable to have the lipolytic polypeptide or enzyme in a substantially pure form. Similarly, it may be desirable to have the lipolytic polypeptide or enzyme in an essentially pure form.

It should be understood that the source of the lipolytic polypeptide or enzyme should be considered in determining the optimal expression host. Additionally, the skilled worker in the field will be capable of selecting the best expression system for a particular gene through routine techniques utilizing the tools available in the art.

One skilled in the art is well aware of methods for introducing polynucleotide sequences into *E. coli* cells, See for example, Andreoli, et al, U.S. Pat. No. 5,278,066. Some published methods for the introduction of DNA constructs into lipase producing strains of *E. coli* include Sanchez, M, et al, *Biotechnol. Bioeng.* 78(3):339-45 (2002); Dartois, V, et al, *Biochim. Biophys. Acta,* 1131(3):253-260 (1992); and Cho, A R, et al, *EMS Microbiol Lett.* 186(2):235-238 (2000), incorporated by reference.

One skilled in the art is well aware of methods for introducing polynucleotide sequences into *Bacillus* cells. See for example, Ferrari et al., Genetics pg 57-72 in Harwood et al. Ed. "*Bacillus*", Plenum Publishing Corp. 1989 wherein methods of transformation, including protoplast transformation and congression; transduction; and protoplast fusion are disclosed. Methods of transformations are particularly preferred to introduce a DNA construct according to the invention into a host cell. In particular methods are also described for *B. subtilis* in Chang et al., *Mol. Gen. Genet* 168:11-115 (1979); for *B. megaterium* in Vorobjeva et al., *FEMS Microbiol. Letters* 7:261-263 (1980); for *B amyloliquefaciens* in Smith et al., *Appl. and Env. Microbiol.* 51:634 (1986); for *B. thuringiensis* in Fisher et al., *Arch. Microbiol.* 139:213-217 (1981); and for *B. sphaericus* in McDonald, *J. Gen. Microbiol.* 130: 203 (1984). Reference is also made to Saunders et al., *J. Bacteriol.* 157:718-726 (1984); Hoch et al., *J. Bacteriol.* 93:1925-1937 (1967); Mann et al., *Current Microbiol.* 13:131-135 (1986); and Holubova, *Folia Microbiol.* 30: 97 (1985).

A preferred general transformation and expression protocol for protease deleted *Bacillus* strains is provided in Ferrari et al., U.S. Pat. No. 5,264,366, incorporated herein by reference. Transformation and expression in *Aspergillus* is described in, for example, Berka et al., U.S. Pat. No. 5,364,770, incorporated herein by reference.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138), all incorporated herein by reference, and may be adapted for the introduction of a DNA construct encoding a lipolytic polypeptide or enzyme.

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of the promoter sequences. Large batches of transformed cells can be cultured as described below. Finally, product is recovered from the culture using standard techniques.

Thus, the invention herein provides for the expression and enhanced secretion of the inventive lipolytic polypeptides or enzyme whose expression is under control of promoter sequences, fusion DNA sequences, and various heterologous constructs. The invention also provides processes for expressing and secreting high levels of the inventive lipolytic polypeptides or enzyme(s).

C. Methods for Expressing a Lipolytic Enzyme

The methods of the invention rely on the use cells to express a lipolytic polypeptide or enzyme, with no particular method of expression required.

The invention provides host cells that have been transduced, transformed or transfected with an expression vector comprising a lipolytic polypeptide or enzyme-encoding nucleic acid sequence. The culture conditions, such as temperature, pH and the like, are those previously used for the parental host cell prior to transduction, transformation or transfection and will be apparent to those skilled in the art.

In one approach, a bacterial, fungal or yeast cell is transfected with an expression vector having a promoter or biologically active promoter fragment or one or more (e.g., a series) of enhancers which functions in the host cell line, operably linked to a DNA segment encoding a lipolytic polypeptide or enzyme, such that the lipolytic polypeptide or enzyme is expressed in the cell line.

Thus, the present invention provides host cells comprising cells which have been modified, selected and cultured in a manner effective to result in lipolytic polypeptide or enzyme production or expression relative to the corresponding non-transformed parental cell.

Host cells expressing a lipolytic polypeptide or enzyme are cultured under conditions typically employed to culture the parental cell line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of lipolytic polypeptide or enzyme expression are achieved.

Preferred culture conditions for a given host cell may be found in the scientific literature and/or from the source of the fungi such as the American Type Culture Collection (ATCC; <www.atcc.org>). After cell growth has been established, the cells are exposed to conditions effective to cause or permit the expression of a lipolytic polypeptide or enzyme.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of an *Aspergillus* sp. gene may be used which if lacking in the host strain results in the host strain displaying an auxotrophic phenotype.

Although the following discusses the *Aspergillus* system, similar procedures for *Trichoderma* and other fungal systems, as well as bacterial systems, may be used as will be appreciated by one skilled in the art.

DNA encoding the lipolytic polypeptide or enzyme is then prepared for insertion into an appropriate microorganism. According to the present invention, DNA encoding a lipolytic polypeptide or enzyme comprises the DNA necessary to encode for a protein that has functional lipolytic activity. The DNA fragment encoding the lipolytic polypeptide or enzyme may be functionally attached to a promoter sequence, for example, the fungal promoter of the glaA gene or the bacterial promoter of the aprE gene.

It is also contemplated that more than one copy of DNA encoding a lipolytic polypeptide or enzyme may be recombined into the strain to facilitate overexpression. The DNA encoding the lipolytic polypeptide or enzyme may be prepared by the construction of an expression vector carrying the DNA encoding the lipolytic polypeptide or enzyme. The expression vector carrying the inserted DNA fragment encoding the lipolytic polypeptide or enzyme may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pRAX is such a general-purpose fungal expression vector. Genes or part thereof can be inserted downstream of the strong glaA promoter. An example of an integrative expression vector is the pTrex vector. Genes or part thereof can be inserted downstream of the strong cbh1 promoter.

In the vector, the DNA sequence encoding the lipolytic polypeptide or enzyme of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the lipolytic polypeptide or enzyme. The DNA encoding the signal sequence is preferably that which is naturally associated with the gene to be expressed, however the signal sequence from any suitable source is contemplated in the present invention.

The procedures used to fuse the DNA sequences coding for the lipolytic polypeptide or enzyme of the present invention with the promoter into suitable vectors are well known in the art.

D. Methods of Analysis For Lipolytic Enzyme Nucleic Acid Coding Sequences and/or Protein Expression.

In order to evaluate the expression of a lipolytic polypeptide or enzyme by a cell line that has been transformed with a lipolytic polypeptide or enzyme-encoding nucleic acid construct, assays can be carried out at the protein level, the RNA level or by use of functional bioassays particular to lipolytic activity and/or lipolytic polypeptide or enzyme production.

In general, assays employed to analyze the expression of a lipolytic polypeptide or enzyme include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a lipolytic polypeptide or enzyme may be measured in a sample directly, for example, by assays for lipolytic activity, expression and/or production. Such assays are described, for example, See, for example, Gupta et al, Biotechnol. Appl. Biochem. (2003) 37:63-71, Andre, Christophe, et al, U.S. Pat. No. 5,990,069 (International Publication WO 96/18729A1). which are expressly incorporated by reference herein.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a lipolytic polypeptide or enzyme. The details of such methods are known to those of skill in the art and many reagents for practicing such methods are commercially available.

V. Protein Expression

Proteins of the present invention are produced by culturing cells transformed with an expression vector containing the inventive lipolytic polypeptide or enzyme gene whose expression is under control of promoter sequences. The present invention is particularly useful for enhancing the intracellular and/or extracellular production of polypeptides or enzymes. The polypeptides or enzymes may be homologous or heterologous.

Polypeptides or enzymes of the present invention may also be modified in a way to form chimeric molecules comprising a polypeptide or enzyme of interest fused to another, heterologous polypeptide or amino acid sequence. In one embodiment, such a chimeric molecule comprises a fusion of the polypeptide or enzyme of interest with a tag polypeptide which provides an epitope to which an anti-tag antibody can selectively bind. The epitope tag is generally placed at the amino-or carboxyl-terminus of the polypeptide or enzyme of interest.

Various tag polypeptides/enzymes and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field et al, *Mol. Cell. Biol.* 8:2159-2165 (1988)); the c-myc tag and the 8F9, 3C7, 6E10, G4, B7 and 9E10 antibodies thereto (Evan et al., *Molecular and Cellular Biology* 5:3610-3616 (1985)); and the Herpes Simplex virus glycoprotein D (gD) tag and its antibody (Paborsky et al., Protein Engineering 3(6):547-553 (1990)). Other tag polypeptides include the FLAG-peptide (Hopp et al., *BioTechnology* 6:1204-1210 (1988)); the KT3 epitope peptide (Martin et al., *Science* 255:192-194 (1992)); tubulin epitope peptide (Skinner et al., *J. Biol. Chem.* 266:15163-15166 (1991)); and the T7 gene 10 protein peptide tag (Lutz-Freyermuth et al., *Proc. Natl. Acad. Sci. USA* 87:6393-6397 (1990)).

Conditions appropriate for expression of said ELIP gene comprises providing to the culture the components necessary for growth and/or expression of the inventive lipolytic polypeptide or enzyme. Optimal conditions for the production of the polypeptides or enzymes will vary with the choice of the host cell, and with the choice of protein to be expressed. Such conditions will be easily ascertained by one skilled in the art through routine experimentation or optimization.

E. Methods for Purifying a Lipolytic Enzyme

In general, a lipolytic polypeptide or enzyme produced in cell culture is secreted into the medium and may be purified or isolated, e.g., by removing unwanted components from the cell culture medium. However, in some cases, a lipolytic polypeptide or enzyme may be produced in a cellular form necessitating recovery from a cell lysate. In such cases the lipolytic polypeptide or enzyme is purified from the cells in which it was produced using techniques routinely employed by those of skill in the art. Examples include, but are not limited to, affinity chromatography (Tilbeurgh et al, 1984), ion-exchange chromatographic methods (Goyal et al., 1991; Fliess et al, 1983; Bhikhabhai et al., 1984; Ellouz et al., 1987), including ion-exchange using materials with high resolution power (Medve et al, 1998), hydrophobic interaction chromatography (Tomaz and Queiroz, 1999), and two-phase partitioning (Brumbauer, et al., 1999).

The polypeptide or enzyme of interest is typically purified or isolated after expression. The polypeptide or enzyme of interest may be isolated or purified in a variety of ways known to those skilled in the art depending on what other components are present in the sample.

Typically, the lipolytic polypeptide or enzyme is fractionated to segregate polypeptides or enzymes having selected properties, such as binding affinity to particular binding agents, e.g., antibodies or receptors; or which have a selected molecular weight range, or range of isoelectric points.

Once expression of a given lipolytic polypeptide or enzyme is achieved, the lipolytic polypeptide or enzyme thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75.

Standard purification methods include electrophoretic, molecular, immunological and chromatographic techniques, including ion exchange, hydrophobic, affinity, and reverse-phase HPLC chromatography, and chromatofocusing. For example, the polypeptide or enzyme of interest may be purified using a standard anti-polypeptide or enzyme of interest antibody column. Ultrafiltration and diafiltration techniques, in conjunction with polypeptide or enzyme concentration, are also useful. For general guidance in suitable purification techniques, see Scopes, Protein Purification (1982). The degree of purification necessary will vary depending on the use of the polypeptide or enzyme of interest. In some instances no purification will be necessary.

VI. Utility of Lipolytic Enzymes

According to the invention, an inventive lipolytic polypeptide or enzyme of the invention may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) or U.S. Pat. No. 4,689,297 (to Genencor Intl.) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. The inventive lipolytic polypeptides or enzymes may be encapsulated, for example, using the methods described in U.S. Pat No. 6,420,333. Examples of film-forming coating materials suitable for application by fluid bed techniques are given in patent GB 1483591. Liquid enzyme preparations may, for example, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. The detergent compositions according to the invention can be used depending on their formulation as a washing powder, granule or liquid to wash fabrics; as a spot-removing product to remove spots or degrease objects or to remove spots from fabric before cleaning; and as a powder or granular liquid for dishwashing. A liquid detergent may be aqueous, typically containing up to 70% water and 0-30% organic solvent, or nonaqueous.

The detergent composition comprises one or more surfactants, each of which may be anionic, nonionic, cationic, or zwitterionic. The detergent will usually contain 0-50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as an amylase, a pullulanase, a cutinase, a protease, a cellulase, a peroxidase, an oxidase, (e.g. laccase) and/or another lipase.

The detergent may contain 1-65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzene-sulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, ant-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7-11.

A lipolytic polypeptide or enzyme of the invention may be incorporated in concentrations conventionally employed in detergents. It is at present contemplated that, in a detergent composition of the invention, an inventive lipolytic polypeptide or enzyme may be added in an amount corresponding to 0.00001-1 mg (calculated as pure enzyme protein) of the lipolytic polypeptide or enzyme per liter of wash liquor.

The detergent compositions of this invention may employ besides the lipolytic polypeptide or enzyme composition, a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The lipolytic polypeptide or enzyme composition as described above can be added to the detergent composition either in a liquid diluent, in granules, in emulsions, in gels, in pastes, and the like. Such forms are well known to the skilled artisan. When a solid detergent composition is employed, the lipolytic polypeptide or enzyme composition is preferably formulated as granules. Preferably, the granules can be formulated so as to contain a lipolytic polypeptide or enzyme protecting agent.

Preferably the lipolytic polypeptide or enzyme compositions are employed from about 0.05 weight percent to about 5 weight percent relative to the total detergent composition. More preferably, the lipolytic polypeptide or enzyme compositions are employed from about 0.2 weight percent to about 5 weight percent relative to the total detergent composition.

In addition the desired lipolytic polypeptide or enzyme nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

A purified form of a lipolytic polypeptide or enzyme may be used to produce either monoclonal or polyclonal antibodies specific to the expressed protein for use in various immunoassays. (See, e.g., Hu et al, 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of lipolytic polypeptides or enzymes.

EXAMPLES

The present invention is described in further detail in the following examples which are not in any way intended to limit the scope of the invention as claimed. The-attached Figures are meant to be considered as integral parts of the specification and description of the invention. All references cited are herein specifically incorporated by reference for all that is described therein.

Example 1

Sample Collection and Processing

This example illustrates how to collect samples and process them to obtain sufficient DNA to create a cDNA library.

Samples of water and sediment (250 ml) were collected from the littoral zone of Lake Elmenteita, Kenya using a 250-ml stainless steel beaker mounted on the end of a flexible extendible 1-m pole and placed in sealable plastic containers (Whirlpak) for transport to the laboratory at ambient temperature. The pH of the samples was 10 to 10.5 with a temperature 23° C. to 27° C., and a conductivity of 10.69-11.00 mS cm$^{-1}$.

To collect the microbial flora, water (350-750 ml) from the lakes was filtered on site (using a hand operated vacuum pump) through a sequence of sterile membrane filters (47 mm diameter), composed of cellulose nitrate or cellulose acetate, of decreasing pore size, until all water flow stopped. The sequence of filters was 8 μm, 3 μm and 0.22 μm. The individual membrane filters were placed immediately into 10 ml of cold, sterile cell stabilization buffer (TES) containing 10 mM Tris HCl, pH8.0; 1 mM EDTA and 5% w/v NaCl in 30 ml sterile plastic universal tubes and kept on ice in a refrigerated cool box until they could be processed further, usually within 4 hours of sampling. The microbial material on the filters was dispersed by vigorous vortex mixing with sterile glass beads (5 ml) and the cells pelleted in microfuge tubes by centrifugation at 13,000 g for 5 min. The microbial material was aliquoted to the microfuge tubes in volumes estimated to contain the equivalent of $10^8$ to $10^9$ bacterial cells, giving a total of 12 tubes. The DNA was extracted using the GenomicPrep™ Cells and Tissue DNA isolation kit (Amersham Pharmacia biotech, Piscataway, N.J., USA) following the manufacturer's instructions. Cells in each tube were resuspended in 600 μl of the Cell Lysis Solution provided, and incubated at 80° C. for 5 min to lyse the cells. Samples prepared by this method are stable at room temperature for at least 18 months, and were transported back to the laboratory in this form. DNA extraction was completed by RNase A treatment, protein precipitation and isopropanol precipitation of the DNA following the manufacturer's protocol. Each DNA pellet was dissolved in 100 µl sterile Tris buffer 10 mM pH 8.5.

DNA yield was estimated by running 5 µl samples on a 0.5% w/v agarose gel and comparing with known amounts of bacterial genomic DNA. The samples were pooled, giving a total of about 20 µg DNA. When lower yields were encountered, the material was supplemented with about 30-50% extra DNA extracted from the water samples which were collected at the same time as the on-site material and stored at 4° C. in the laboratory until required. In this case the microbial mass was pelleted by centrifugation. DNA isolation was carried out as described above, except that incubation with 50 µl lysozyme solution (50 mg ml$^{-1}$ in 10 mM Tris-HCl pH 8, 1 mM EDTA) for 30 minutes at 37° C. preceded the addition of the lysis solution, in order to degrade Gram positive cell walls. About 30 µg DNA was the amount of starting material that preliminary experiments had shown was needed to carry out the trial and bulk restriction digestion and size fractionation to give sufficient material for library construction.

Selective Enrichment Culture

Selective enrichment culture from Lake Elmenteita was prepared by adding 1 ml of pooled samples of water and sediment to 200 ml of a sterile alkaline minimal medium. The lipase selective medium contained, in g per litre, 1 g Yeast extract (Difco), 1 g $K_2HPO_4$, 0.2 g $MgSO_4.7H_2O$, 10 g $Na_2CO_3$, 40 g NaCl and 10% v/v olive oil. Cultures were grown at 37° C. for 3-5 days until bacterial growth was clearly visible. Cells were obtained by centrifugation and DNA was extracted according to the method of Pitcher et al., (Pitcher D G, Saunders N A, Owen R J (1989). Rapid extraction of bacterial genomic DNA with guanidium thiocyanate. Letters in Applied Microbiology 8: 151-156).

Example 2

Library Construction

The following example details how to prepare a DNA library for use in screening and detection of novel sequences in *E. coli*.

Preparation of DNA

The pooled DNA was used for construction of the genomic DNA library. The purified DNA was partially digested with Sau3A1 to give an average fragment size in the range 2-10 kb. Restricted DNA was size fractionated by electrophoresis on 0.5% agarose in TAE (0.04M Tris-acetate, 0.001M EDTA pH 8.0). Material in the 2 to 10 kb range was excised and replaced in a well of the same size cut in an unused part of the agarose gel and concentrated to a narrow band by reversed electrical current. The DNA band was excised and DNA extracted using the QIAGEN (Crawley, UK) QIAEXII gel extraction kit, following the manufacturer's guidelines. The eluted DNA was precipitated with ethanol and resuspended in 10 mM Tris HCl buffer, pH 8.5.

Preparation of Lambda Libraries

The restricted DNA was cloned into a Lambda vector using the ZAP-Express™ vector kit (predigested with BamH1 and alkaline phosphatase treated) and the Gigapak® III Gold packaging extract (Stratagene, Amsterdam, The Netherlands) following the manufacturer's protocol. The primary libraries were amplified as per protocol by plating aliquots containing ~5×10$^4$ pfu with host *E. coli* strain XL1-Blue MRF' on 150 mm Petri dishes and eluting the phage in buffer. Amplified libraries were stored in 7% v/v dimethyl sulphoxide at −80° C. after freezing in liquid nitrogen. Primary titres were generally ≧10$^6$ pfu, and after amplification ≧10$^9$ pfu ml$^{-1}$.

Assessment of Library Quality

The phagemid vector pBK-CMV was excised from the Lambda ZAP library using ExAssist helper phage (Stratagene) as described by the manufacturer, and used to infect *E. coli* strain XLOLR. Plasmid-containing clones were isolated by plating on Luria—Bertani (LB) agar containing 50 µg ml$^{-1}$ kanamycin. Blue:white screening in the presence of Xgal [5-bromo-4-chloro-3-indoyl-β-D-galactoside] and IPTG [isopropylthio-β-D-galactoside] was used to determine cloning efficiency. If no DNA has been cloned into the Lambda vector, the β-galactosidase gene is expressed in the presence of the inducer IPTG, resulting in cleavage of the substrate analogue Xgal to produce a blue pigment in the colony. If however a fragment of the genomic DNA has been successfully cloned into the Lambda vector it disrupts the gene so that no enzyme is produced and the colony remains white. The ratio of blue to white colonies therefore can be used to calculate the percentage of clones containing an insert. Twenty four colonies were selected at random and plasmid DNA prepared using the Wizard®Plus SV Miniprep DNA purification system (Promega UK, Southampton) Restriction analysis using Pst1 and HindIII which flank the BamH1 cloning site followed by agarose gel electrophoresis was used to determine insert sizes. >90% of the clones contained inserts in the 2-10 Kb size range.

Example 3

Library Screening for Esterase/Lipase

DNA libraries in the pBK-CMV phagemid were screened for esterase/lipase activity in a plate assay of the *E. coli* clones. To detect esterase/lipase activity the genomic libraries were plated on LB agar containing kanamycin (50 µg ml$^{-1}$), and after growth replica-plated onto tributyrin agar (Oxoid) containing IPTG (15 µl of a 0.5 M solution spread on the surface of the agar in a 7 cm diameter Petri dish). Positive clones were identified by the faint zone of clearing around them.

Screening of the Lake Elmenteita environmental library for lipase activity gave one positive clone (ELIP) in 100,000 screened, see Table 1. The insert size was estimated at 4.5 kb. Sequencing by primer walking showed that it comprised 4313 bp, encoding two major putative ORFs. One encoding 402 amino acids, see FIG. 3, gave highest homology of the translated protein sequence to a putative carboxylesterase from *Salmonella typhymurium* LT2 (NCBI entrez NP_460582.1), having 67% identity over 402 amino acids. It therefore is a strong candidate for the lipase/esterase activity. The second was 326 amino acids long, and had highest identity (53% over 305 amino acids) to a probable pyridoxal phosphate aminotransferase protein (NP_520132.1) from *Ralstonia solanacearum*.

Table 1 summarises the libraries from which enzyme activities described here have been discovered, including the names of the library, incidence of positive clones, name of clone, size of cloned insert, size of predicted protein and identity to proteins present in the data bases.

TABLE 1

Details of the esterase/lipase clone libraries

| Library screened | Incidence of positive clones | Name of clones sequenced | Cloned insert size bp | ORF Information |
|---|---|---|---|---|
| Lake Elmenteita environmental | 1/100,000 | ELIP | 4313 | 1209 bp, 402 aa, 67% identity *S. typhimurium* NP_460582.1 |
| Lake Elmenteita selective olive oil enrichment | 1/30,000 | LIP1 | 2285 | 792 bp, 263 aa, 42% identity *V. cholerae* NP_232345. |
|  |  | LIP2 | 3112 | 645 bp, 214 aa 43% identity *E. coli* U82664 |

The incidence of positive clones (Table 1) demonstrates that biasing an environmental sample to express a particular enzyme activity by enrichment culture does indeed result in an increased frequency for isolating that enzyme activity by more than 3-fold.

Example 4

Characterisation of the Esterase/Lipase-Positive Clones

Plasmid DNA was isolated from three esterase/lipase-positive clones, and the size of the inserts determined by restriction digestion as described above. DNA sequencing of the plasmid DNA (using primer sites in the pBKCMV plasmid) was carried out by the Protein and Nucleic Acid Chemistry Laboratory at Leicester University, using the Perkin Elmer 'BigDye' terminator chemistry and the model 377 ABI automated DNA sequencer. Complete coverage of the sequence was obtained by 'primer walking' from both the 5' and 3' ends of the insert. The sequence was edited using Applied Biosystems multisequence editor Seqed™ version 1.0.3. Sequence was assembled with programmes in the GCG Wisconsin Package, version 10.2-UNIX, available at the University of Leicester. Comparison of sequences to those in the databases was made using BLASTX 2.1.3 and ORF finder was used to identify possible open reading frames. The nucleotide sequence of the inserted environmental DNA in an esterase/lipase-positive clones is shown in FIG. 1.

Comparison of the inserted environmental DNA sequence to protein sequences in the databases was made using the BLASTX program.

Example 5

Identification of Esterase/Lipase Genes

Possible Open Reading Frames (ORF) in the nucleotide sequence of the inserted environmental DNA of 3 clones were identified using the ORF Find facility of the MapDraw program (DNASTAR, Brighton, Mass., USA) or ORF Search from the Vector NTI Suite of programs (InforMax®, North Bethesda, Md., USA). The results are recorded in FIG. 4.

The identified ORF's were examined by BLAST programs. The coding region for ELIP is shown in FIG. 2.

An examination of the ORF nucleotide sequences using the BLASTx program, which compares the six-frame conceptual translation products of a nucleotide query sequence (both strands) against a protein sequence database, revealed surprisingly, very low similarity (42-67%) to a number of putative bacterial esterases. It is very probable that enzymes with homology this low would not have been detected using convention methods using DNA probes based on known esterase/lipase gene sequences, especially given the very high diversity of esterases/lipases already characterised.

The translated protein sequences of the esterase/lipase coding regions are shown in FIG. 3.

Of the esterase/lipase enzymes described here, ELIP is most closely related to the carboxyesterase type B family having a catalytic triad of serine, a glutamate or aspartate and a histidine. It contains the sequence FGGDAGNVTLFGE-SAG (SEQ ID NO:4) highlighted in the degenerate sequence motif characteristic of this family, F-[GR]-G-x-x-x-x-[LIVM]-x-[LIV]-x-G-x-S-[STAG]-G (SEQ ID NO:5) (Prosite PDOC00112).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A substantially pure polypeptide, wherein said polypeptide comprises an amino acid sequence having at least 93% amino acid sequence identity with the amino acid sequence set forth in SEQ ID NO.:3, wherein said polypeptide has lipolytic activity.

2. The polypeptide of claim 1, wherein said polypeptide comprises an amino acid sequence having at least 95% sequence identity with the amino acid sequence set forth in SEQ ID NO.:3.

3. The polypeptide of claim 1, wherein said polypeptide comprises an amino acid sequence having at least 97% sequence identity with the amino acid sequence set forth in SEQ ID NO.:3.

4. The polypeptide of claim 1, wherein said polypeptide comprises an amino acid sequence having at least 93% sequence identity with the amino acid sequence set forth in SEQ ID NO.:3 and is encoded by a polynucleotide having a nucleic acid sequence having at least 93% nucleic acid sequence identity with the nucleic acid sequence set forth in SEQ ID NO.:1.

5. A detergent composition comprising the polypeptide of claim 1.

* * * * *